(12) United States Patent
Sugiyama et al.

(10) Patent No.: US 10,215,604 B2
(45) Date of Patent: Feb. 26, 2019

(54) FLUID ANALYSIS SYSTEM WITH DENSITOMETER HAVING ELECTRICALLY ISOLATED VIBRATING TUBE

(71) Applicant: SCHLUMBERGER TECHNOLOGY CORPORATION, Sugar Land, TX (US)

(72) Inventors: Hitoshi Sugiyama, Sagamihara (JP); Christopher Harrison, Auburndale, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 128 days.

(21) Appl. No.: 14/947,565

(22) Filed: Nov. 20, 2015

(65) Prior Publication Data

US 2017/0146688 A1 May 25, 2017

(51) Int. Cl.
*G01F 1/84* (2006.01)
*G01N 9/00* (2006.01)
(Continued)

(52) U.S. Cl.
CPC .......... *G01F 1/8472* (2013.01); *E21B 47/102* (2013.01); *E21B 49/10* (2013.01);
(Continued)

(58) Field of Classification Search
CPC .............. E21B 2049/085; G01N 9/002; G01N 2009/004; G01N 2009/006; G01N 27/74; G01N 2011/0086; G01N 2291/02818; G01F 1/8472; G01F 1/32; G01V 9/00; C03C 29/00; F16L 25/02; F16L 25/025; F16L 25/03

USPC ................ 73/861.355, 32 A, 152.05–152.07, 73/152.32, 32 R, 579; 702/54; 174/47, 174/168–175, 152 GM, 85, 167, 135, 174/138 R, 138 G, 142, 148, 149 R; 439/192; 285/53–54

See application file for complete search history.

(56) References Cited

U.S. PATENT DOCUMENTS 2,257,385 A * 9/1941 Keegan ................... F24H 1/186
122/13.01
4,417,913 A * 11/1983 Davis ........................ C03C 8/04
174/50.61
(Continued)

FOREIGN PATENT DOCUMENTS

WO WO 2014066433 A1 * 5/2014 ........... G01N 29/036
WO 2014158376 A1 10/2014

OTHER PUBLICATIONS

Coleou et al, A microfluidic oscillating tube densitometer, Rev. Sci. Instrum. 80, 105101 2009.*
(Continued)

*Primary Examiner* — Daniel S Larkin
*Assistant Examiner* — David L Singer

(57) ABSTRACT

A vibrating-tube fluid measurement device includes a tube, a base block, a magnet which applies a magnetic field to the tube, an excitation source which generates vibration of the tube, a vibration sensor which measures a signal corresponding to a vibration frequency of the tube, and an electrical isolator formed of glass, wherein the vibrating tube is mounted to a base block via the electrical isolator and electrically isolated from the base block via the electrical isolator.

24 Claims, 13 Drawing Sheets

(51) Int. Cl.
*E21B 47/10* (2012.01)
*E21B 49/08* (2006.01)
*E21B 49/10* (2006.01)

(52) U.S. Cl.
CPC .......... *G01F 1/8409* (2013.01); *G01F 1/8413* (2013.01); *G01F 1/8481* (2013.01); *G01N 9/002* (2013.01); *E21B 2049/085* (2013.01); *G01N 2009/006* (2013.01); *G01N 2291/02818* (2013.01); *G01N 2291/02836* (2013.01)

(56) References Cited

U.S. PATENT DOCUMENTS

| | | | | |
|---|---|---|---|---|
| 4,655,075 | A * | 4/1987 | Albert | G01N 9/002 73/32 A |
| 4,678,358 | A * | 7/1987 | Layher | C03C 27/02 174/152 GM |
| 4,994,671 | A | 2/1991 | Safinya et al. | |
| 6,347,293 | B1 * | 2/2002 | Cunningham | G01F 1/8413 702/100 |
| 6,425,168 | B1 * | 7/2002 | Takaku | H01L 21/67306 118/500 |
| 7,384,453 | B2 | 6/2008 | Bostrom et al. | |
| 7,575,681 | B2 | 8/2009 | Angelescu et al. | |
| 7,637,151 | B2 | 12/2009 | Raghuraman et al. | |
| 8,028,562 | B2 | 10/2011 | Shah et al. | |
| 8,262,909 | B2 | 9/2012 | Angelescu et al. | |
| 8,910,514 | B2 | 12/2014 | Sullivan et al. | |
| 9,638,681 | B2 | 5/2017 | Zhdaneev et al. | |
| 2003/0175411 | A1 * | 9/2003 | Kodas | C09D 11/30 427/58 |
| 2006/0213552 | A1 * | 9/2006 | Sparks | B60T 17/18 137/2 |
| 2006/0243066 | A1 * | 11/2006 | Mehendale | G01F 1/8422 73/861.353 |
| 2010/0265492 | A1 | 10/2010 | Schroeder et al. | |
| 2010/0268469 | A1 | 10/2010 | Harrison et al. | |
| 2014/0260586 | A1 | 9/2014 | Van Hal et al. | |

OTHER PUBLICATIONS

Vici Valco Cheminert Catalog, 2009.*
Mullins, Synthesis and Processing of Nanostructured Materials, 2009, Abstract of Manufacturing of Doped Glasses using Reactive Electrophoretic Deposition (REPD).*
Pecht et al, Quality Conformance and Qualification of Microelectronic Packages and Interconnects, 1994, pp. 320-321.*
Collins English Dictionary Definitions: Base; and Block.*
Professional Plastics, Micarta Laminates—Various Grades Technical Information, 2001.*
Professor Garanin, "Physics of Sound: 3—Standing waves, overtones series", Spring 2007 for Physics 140.*

* cited by examiner (Section A-A)

(Section B)

(Section C)

FLUID ANALYSIS SYSTEM WITH DENSITOMETER HAVING ELECTRICALLY ISOLATED VIBRATING TUBE

BACKGROUND

The oil and gas industry has developed various tools capable of determining formation fluid properties. For example, borehole fluid sampling and testing tools such as Schlumberger's Modular Formation Dynamics Testing (MDT) Tool can provide important information on the type and properties of reservoir fluids in addition to providing measurements of reservoir pressure, permeability, and mobility. These tools may perform measurements of the fluid properties downhole, using sensor modules on board the tools. These tools can also withdraw fluid samples from the reservoir that can be collected in bottles and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes, resins, and various other impurity concentrations.

The reservoir fluid may break phase in the reservoir itself during production. For example, one zone of the reservoir may contain oil with dissolved gas. During production, the reservoir pressure may drop to the extent that the bubble point pressure is reached, allowing gas to emerge from the oil, causing production concerns. Knowledge of this bubble point pressure may be helpful when designing production strategies.

Characterizing a fluid in a laboratory utilizes an arsenal of devices, procedures, trained personnel, and laboratory space. Successfully characterizing a fluid in a wellbore uses methods, apparatus, and systems configured to perform similarly with less space and personal attention and to survive in conditions that quickly destroy traditional lab equipment. Identifying the undesired phase change properties of a fluid is especially useful when managing a hydrocarbon reservoir.

SUMMARY

In accordance with example embodiments, a device for measuring a property of a fluid sample includes: a tube configured to receive the fluid sample; a base block; a magnet; an excitation source configured to generate vibration of the tube when the fluid sample is received in the tube such that a circulation of an electrical current along a portion of the tube is subjected to at least one magnetic field produced by the magnet; a vibration sensor configured to measure a signal corresponding to a vibration frequency of the tube, the vibration frequency varying as a function of, e.g., the density of the fluid sample; and an electrical isolator comprised of glass, wherein the tube is hermetically sealed to the base block via the electrical isolator and electrically isolated from the base block via the electrical isolator.

In accordance with example embodiments, a system for characterizing a fluid includes: a phase transition cell configured to receive the fluid; a piston configured to control pressure of the fluid; a pressure gauge configured to measure the pressure of the fluid and to provide information to control the piston; and a densitometer configured to measure density of the fluid. The densitometer includes: a tube configured to receive a fluid sample; a base block; a magnet; an excitation source configured to generate vibration of the tube when the fluid sample is received in the tube such that a circulation of an electrical current along a portion of the tube is subjected to at least one magnetic field produced by a magnet; a vibration sensor configured to measure a signal corresponding to vibrations of the tube, and an electrical isolator comprised of glass, wherein the tube is mounted to the base block via the electrical isolator and electrically isolated from the base block via the electrical isolator.

In accordance with example embodiments, a method includes: placing a doped glass material in a base block; inserting a hollow tube into the doped glass material; heating the doped glass material to a temperature at which the doped glass material melts; allowing the doped glass material to cool to form a solid glass isolator that mechanically supports the hollow tube with respect to the base block and electrically isolates the hollow tube from the base block.

Further features and aspects of example embodiments of the present invention are described in more detail below with reference to the appended Figures.

FIGURES

DESCRIPTION

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and detailed description, each numerical value should be read once as modified by the term "about" (unless already expressly so modified), and then read again as not so modified unless otherwise indicated in context. Also, in the summary and detailed description, it should be understood that a concentration range listed or described as being useful, suitable, or the like, is intended that any concentration within the range, including the end points, is to be considered as having been stated. For example, "a range of from 1 to 10" is to be read as indicating each possible number along the continuum between about 1 and about 10. Thus, even if specific data points within the range, or even no data points within the range, are explicitly identified or refer to a few specific points, it is to be understood that inventors appreciate and understand that any and all data points within the range are to be considered to have been specified, and that inventors possessed knowledge of the entire range and all points within the range.

Figure 1:
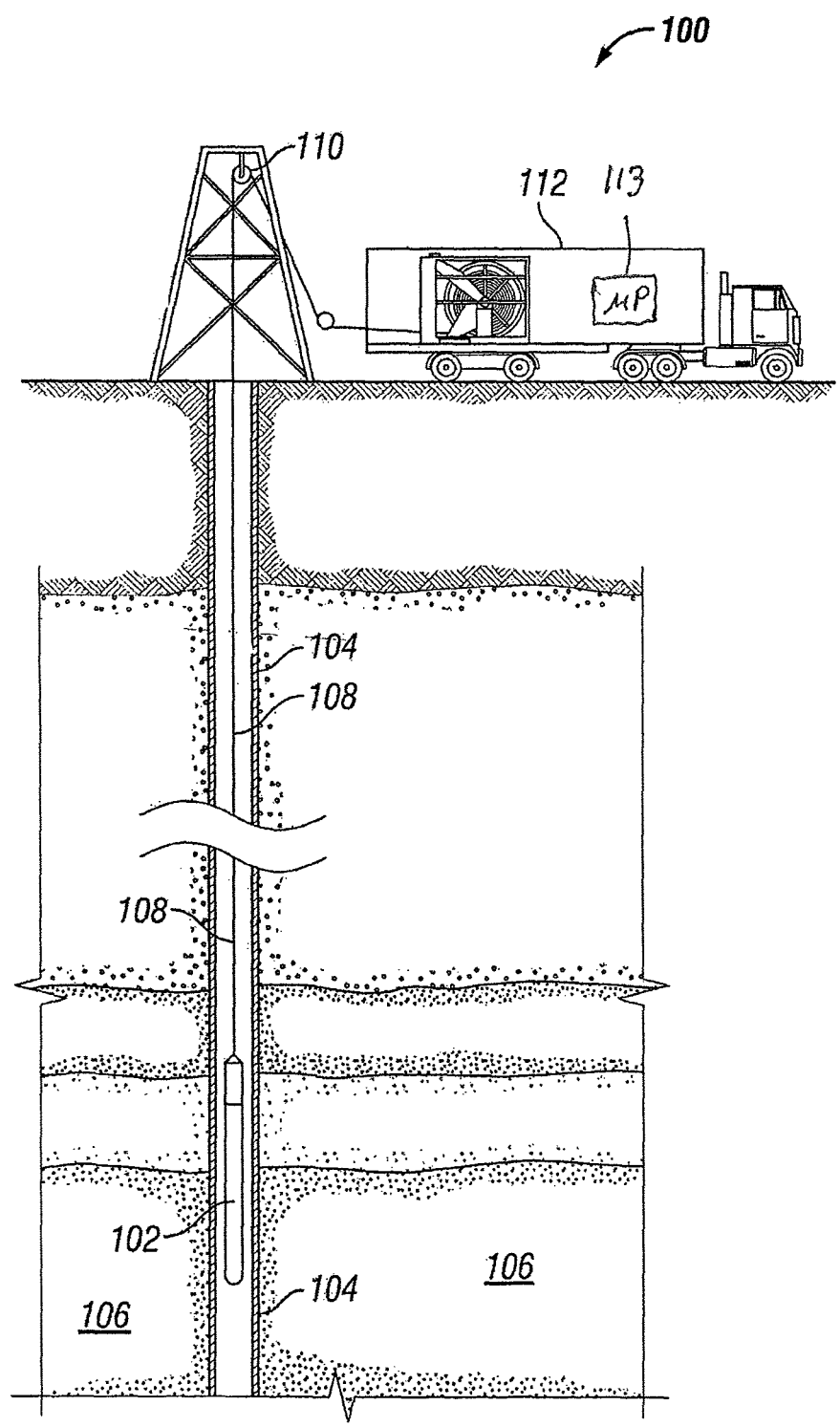
FIG. 1 shows a wireline logging system at a well site in accordance with one embodiment of the present disclosure.

FIG. 1 shows one example of a wireline logging system 100 at a well site. Such a wireline logging system 100 can be used to implement a rapid formation fluid analysis. In this example, a wireline tool 102 is lowered into a wellbore 104 that traverses a formation 106 using a cable 108 and a winch 110. The wireline tool 102 is lowered down into the wellbore 104 and makes a number of measurements of the adjacent formation 106 at a plurality of sampling locations along the wellbore 104. The data from these measurements is communicated through the cable 108 to surface equipment 112, which may include a processing system 113 for storing and processing the data obtained by the wireline tool 102. The surface equipment 112 includes a truck that supports the wireline tool 102. In other embodiments, the surface equipment may be located in other locations, such as within a cabin on an off-shore platform.

Figure 2:
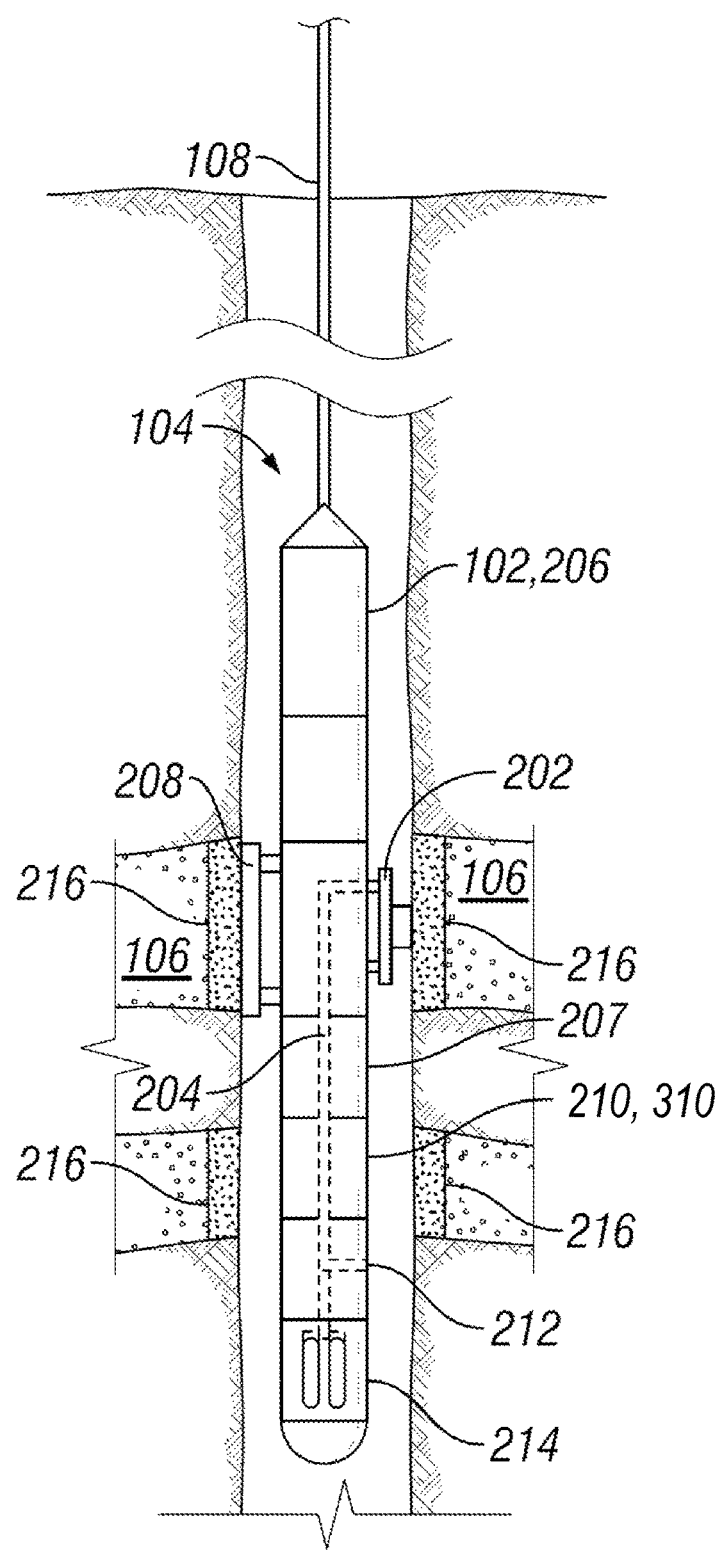
FIG. 2 shows a wireline tool in accordance with one embodiment of the present disclosure.

FIG. 2 shows a more detailed view of the wireline tool 102. The wireline tool 102 includes a selectively extendable fluid admitting assembly (e.g., probe) 202. This assembly 202 extends into the formation 106 and withdraws formation fluid from the formation 216 (e.g., samples the formation). The fluid flows through the assembly 202 and into a main flow line 204 within a housing 206 of the tool 102. A pump module 207 is used to withdraw the formation fluid from the formation 106 and pass the fluid through the flow line 204. The wireline tool 102 may include a selectively extendable tool anchoring member 208 that is arranged to press the probe 202 assembly against the formation 106.

The wireline tool 102 also includes a fluid analyzer module 210 for analyzing at least a portion of the fluid in the flow line 204. This fluid analyzer module 210 is further described below. After the fluid analysis module 210, the formation fluid may be pumped out of the flow line 204 and into the wellbore 104 through a port 212. Some of the formation fluid may also be passed to a fluid collection module 214 that includes chambers for collecting fluid samples and retaining samples of the formation fluid for subsequent transport and testing at the surface (e.g., at a testing facility or laboratory).

Figure 3A:
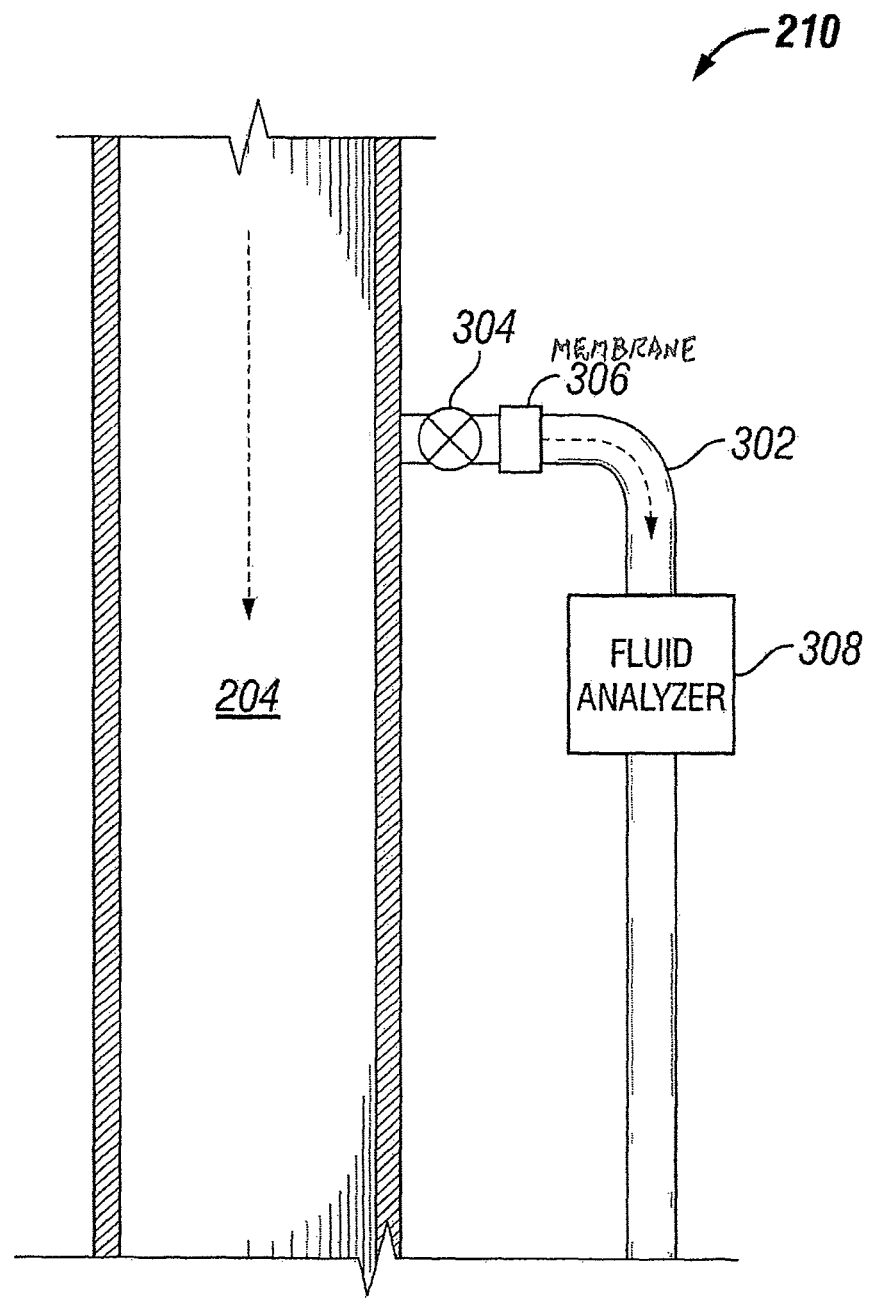
FIG. 3A shows a fluid analyzer module in accordance with one embodiment of the present disclosure.

FIG. 3A shows a more detailed view of a fluid analysis module 210. As shown in FIG. 3A, the fluid analysis module 210 includes a secondary flow line 302 (e.g., a channel) that is coupled through a valve 304 to the main flow line 204. The valve 304 selectively passes a sample of formation fluid into the secondary flow line 302. The secondary flow line 302 also includes a membrane 306 to separate water from the formation fluid sample (e.g., a hydrophobic membrane). Such a membrane is described in U.S. Pat. No. 7,575,681 issued on Aug. 18, 2009 and U.S. Pat. No. 8,262,909 issued on Sep. 11, 2012, each of which is hereby incorporated by reference in its entirety.

In some embodiments, a pump or a piston is used to extract the formation fluid sample from the main flow line 204 and pass the formation fluid through the membrane 306. In various embodiments, the membrane 306 separates water from the formation fluid sample as the sample is being extracted from the main flow line 304. Also, although the membrane 306 is disposed after the valve 304, it should be appreciated that in some embodiments the membrane 306 is disposed before the valve 304. Moreover, although a single membrane 306 is provided in FIG. 3A, it should be understood that some embodiments include multiple membranes.

Once the formation fluid sample passes the membrane 306, the sample flows into a fluid analyzer 308 that analyzes the sample to determine at least one property of the fluid sample. The fluid analyzer 308 is in electronic communication with the surface equipment 112 through, for example, a telemetry module and the cable 108. Accordingly, the data produced by the fluid analyzer 308 can be communicated to the surface for further processing by processing system.

The fluid analyzer 308 can include a number of different devices and systems that analyze the formation fluid sample. For example, in one embodiment, the fluid analyzer 308 includes a spectrometer that uses light to determine a composition of the formation fluid sample. The spectrometer can determine an individual fraction of methane ($C_1$), an individual fraction of ethane ($C_2$), a lumped fraction of alkanes with carbon numbers of three, four, and five ($C_3$-$C_5$), and a lumped fraction of alkanes with a carbon number equal to or greater than six ($C_{6+}$). An example of such a spectrometer is described in U.S. Pat. No. 4,994,671 issued on Feb. 19, 1991 and U.S. Patent Application Publication No. 2010/0265492 published on Oct. 21, 2012, each of which is incorporated herein by reference in its entirety. In some embodiments, the fluid analyzer 308 includes a gas chromatograph that determines a composition of the formation fluid. In some embodiments, the gas chromatograph determines an individual fraction for each alkane within a range of carbon numbers from one to 25 ($C_1$-$C_{25}$). Examples of such gas chromatographs are described in U.S. Pat. No. 8,028,562 issued on Oct. 4, 2011 and U.S. Pat. No. 7,384,453 issued on Jun. 10, 2008, each of which is hereby incorporated by reference in its entirety. The fluid analyzer 308 may also include a mass spectrometer, a visible absorption spectrometer, an infrared absorption spectrometer, a fluorescence spectrometer, a resistivity sensor, a pressure sensor, a temperature sensor, a densitometer, and/or a viscometer. The fluid analyzer 308 may also include combinations of such devices and systems. For example, the fluid analysis module 210 may include a spectrometer followed by a gas chromatograph as described in, for example, U.S. Pat. No. 7,637,151 issued on Dec. 29, 2009 and U.S. patent application Ser. No. 13/249,535 filed on Sep. 30, 2011, each of which is incorporated herein by reference in its entirety.

Figure 3B:
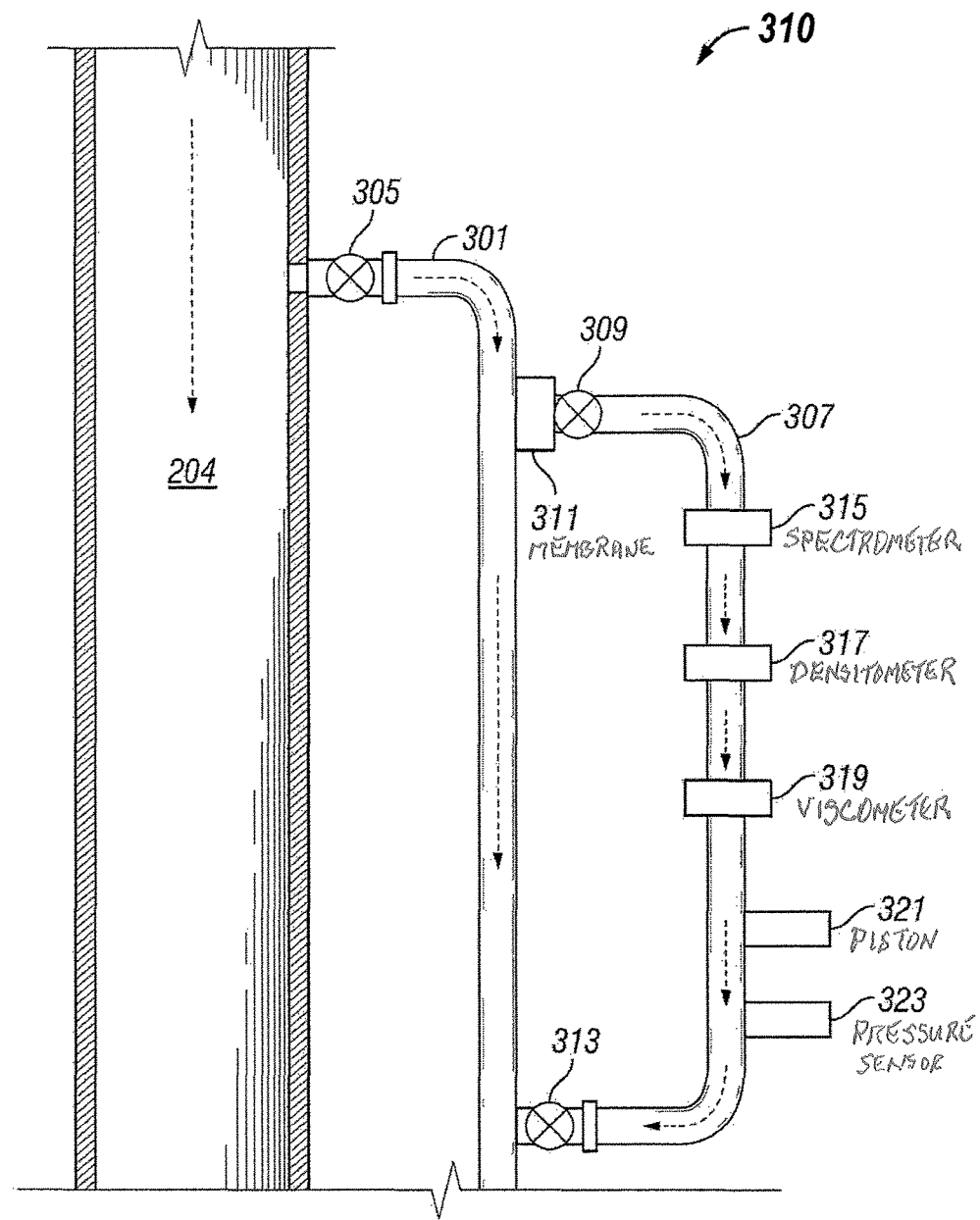
FIG. 3B shows a fluid analyzer module in accordance with another embodiment of the present disclosure.

FIG. 3B shows a fluid analysis module 310 in accordance with another embodiment of the present disclosure. In this example, a bypass flow line 301 is coupled to the main flow line 204 through a first valve 305. The first valve 305 selectively passes formation fluid from the main flow line 204 into the bypass flow line 301. A secondary flow line 307 (e.g., a channel) is coupled through a second valve 309 (e.g., an entrance valve) to the bypass flow line 301. The second valve 309 selectively passes a sample of formation fluid into the secondary flow line 307. The fluid analysis module 310 includes a membrane 311 to separate water from the formation fluid sample (e.g., a hydrophobic membrane). In this embodiment, the membrane 311 is disposed before the second valve 309. The fluid analysis module 310 also includes a third valve 313 (e.g., an exit valve) between the secondary flow line 307 and the bypass flow line 301. The second valve 309 and the third valve 313 can be used to isolate the formation fluid sample within the secondary flow line 307. After analysis, the formation fluid sample can pass to the bypass flow line 301 through the third valve 313.

In the example of FIG. 3B, the fluid analysis module 310 further includes a spectrometer 315 followed by a densitometer 317 and a viscometer 319. Such an arrangement provides both a chemical composition for the fluid sample and physical characteristics for the fluid sample (e.g., density and viscosity). As explained above, other combinations of devices and systems that analyze the formation fluid sample are also possible.

In FIG. 3B, the fluid analysis module 310 also includes a pressure unit 321 for changing the pressure within the fluid sample and a pressure sensor 323 that monitors the pressure of the fluid sample within the secondary flow channel 307. In some embodiments, the pressure unit 321 is a piston that is in communication with the secondary flow line 307 and that expands the volume of the fluid sample to decrease the pressure of the sample. As explained above, the second valve 309 and the third valve 313 can be used to isolate the formation fluid sample within the secondary flow line 307. Also, in some embodiments, the pressure unit 321 can be used to extract the formation fluid sample from the bypass flow line 301 by changing the pressure within the secondary flow line 307. The pressure sensor 323 is used to monitor the pressure of the fluid sample within the secondary flow line 307. The pressure sensor 323 can be a strain gauge or a resonating pressure gauge. By changing the pressure of the fluid sample, the fluid analyzer module 310 can make measurements related to phase transitions of the fluid sample (e.g., bubble point or asphaltene onset pressure measurements). Further details of devices and systems that analyze the formation fluid sample are also provided in PCT Application Publication No. WO 2014/158376 A1, which is hereby incorporated herein by reference in its entirety.

Referring to FIG. 1, near the bottom of the wellbore 104, the pressure may be sufficiently high that the fluid is single-phase. At a given mid-point (the location of which may vary depending on well properties), the pressure may reach the bubble point when the fluid breaks phase, producing gaseous and liquid phases. While the fluid is transiting from the wellbore bottom to the surface, the temperature is monotonically decreasing, increasing the fluid viscosity.

Fluids that may be produced from the formation have their temperature changed as they are brought to the surface, and hence experience a dramatic change in the fluid properties, including but not limited to their density. In order to accurately calculate the flow rate during production, an accurate knowledge of the density as a function of depth is useful. Along with temperature dependence, the fluid pressure may drop below the bubble point while in transit. Some example systems 100 may obtain a fluid sample from the formation and rapidly vary its temperature in order to simulate the fluid's passage through the oil well during the production stage. In some embodiments, the tool 102 may store a sample extracted from the formation after measurements are performed. The tool 102 may be raised to a shallower depth and allow the sample within the PVT device to come to equilibrium, after which additional measurements may be performed. It should be understood that although the tool 102 in the illustrated examples is a wireline tool, the features of the tool 102 may implemented into any suitable apparatus and may be provided to operate in downhole and/or surface locations.

As an example, a description for measuring density will be discussed, with a comparison of the amount of energy to change the sample temperature for both mesoscopic and microfluidic approaches. This would apply as well to a bubble point measurement where one is interested in the temperature dependence as well. The present embodiments may be compared to a conventional viscometer that is macroscopic in size and is directly immersed in the flow-line which has an inner diameter of approximately 5.5 mm. The total amount of fluid to fill the conventional sensors and the surrounding region volume is on the order of 10 milliliters, with an associated heat capacity of, assuming the specific heat of mineral oil, 1.7 Joules/(gram Kelvin), or a heat capacity of approximately 20 Joules/Kelvin. Hence, 20 Joules of energy are removed to reduce the temperature by one degree Kelvin. Furthermore, as the sensors are thermally connected to a large metallic assembly on the order of 1 kilogram (or more), in practice one would reduce the temperature of this assembly as well. Assuming a specific heat of 0.5 Joules/(gram Kelvin) for steel, one would have to remove 500 Joules of energy to reduce the temperature of the whole assembly by one degree. This approach using conventional technologies will be referred to as mesoscopic herein.

As a comparison, microfluidic environments of the present disclosure may use fluid volumes on the order of ten microliters, which corresponds to around 10 milligrams of liquid, which has a heat capacity of about 0.02 Joules/Kelvin (using the above numbers for the specific heat). In practice, one controls the temperature of the microfluidic chamber as well, which may have a mass on the order of 50 grams, and assuming this is fabricated from titanium, with a specific heat of 0.5 Joules/(gram Kelvin), it would use on the order of 25 Joules of energy to change the temperature by one degree. Note that this power usage for the microfluidic approach is 20 times smaller than for mesoscopic approach. Peltier (or thermoelectric) coolers reveals that models with dimensions with the proper scale exist and are specified to produce heat fluxes on the order of 1 Joule/second (1 watt), and one may quickly ramp up or down the temperature of such a device. Hence, a rapid ramping up or down of the temperature of a microfluidic-scale of fluidic volume and associated chamber is feasible.

As indicated above, during a process of sampling fluid into the microfluidic system 210, 310 of the tool 102, a fluid may be sampled from the formation 106. In some embodiments, a small volume (on the order of tens of microliters) of fluid will be sampled, filtered, and passed into the microfluidic system 210, 310. The system 210, 310 may be placed into a pressure compensation system where during the initial phase of its operation, the pressure is approximately 100 psi lower (or less) than the flowline of the tool in which it will be implemented. As discussed above, the microfluidic system 210, 310 may include microfluidic sensors to measure the density, viscosity or any other physical properties of the fluid. The microfluidic system 210, 310 may either be located downhole or at the surface.

For downhole applications, the fluid evaluation may be motivated by the fact that wellbore temperature changes substantially from the formation to the surface. Fluids that are produced from the formation change their temperature accordingly and hence experience a dramatic change in their properties, including but not limited to their density. In order to accurately calculate the flow rate during production one should accurately know the density as a function of depth. This is further complicated by the fact that the fluid may drop below the bubble point while in transit. Hence, a system may be selected that can obtain a fluid sample from the formation and rapidly vary its temperature in order to simulate its passage through the wellbore during the production stage.

Generally, examples disclosed herein relate to collecting a fluid from a wellbore, a fracture in a formation, a body of water or oil or mixture of materials, or other void in a subterranean formation that is large enough from which to collect a sample. The fluid may contain solid particles such as sand, salt crystals, proppant, solid acids, solid or viscous hydrocarbon, viscosity modifiers, weighing agents, completions residue, or drilling debris. The fluid may contain water, salt water, hydrocarbons, drilling mud, emulsions, fracturing fluid, viscosifiers, surfactants, acids, bases, or dissolved gases such as natural gas, carbon dioxide, or nitrogen.

Systems for analyzing these fluids may be located in various locations or environments, including, but not limited to, tools for downhole use, permanent downhole installations, or any surface system that will undergo some combination of elevated pressures, temperatures, and/or shock and vibration. In some embodiments, temperatures may be as high as about 175° C. or about 250° C. with pressures as high as about 25,000 psi.

In general, energy added to a fluid at pressures near the bubble point to overcome the nucleation barrier associated with bubble production. Thus, energy may be added to a fluid thermally through the process of thermal nucleation. The quantity of bubbles produced at the thermodynamic bubble point via thermal nucleation is sufficiently small that their presence is detectable near the place of thermal nucleation in a phase transition cell and not in other components in the measurement system. However, upon further depressurization of the system, the supersaturation becomes large enough that bubble nucleation spontaneously occurs throughout the measurement system. In one or more embodiments, a fluid sample may be depressurized at a rate such that bubble detection may occur in a phase transition cell alone, or may be sufficiently high enough to be detected throughout the overall system.

During depressurization of a sample, the density, viscosity, optical transmission through the phase transition cell, and sample pressure may be simultaneously measured. Depressurization starts at a pressure above the saturation pressure and takes place with a constant change in system volume, a constant change in system pressure, or discreet pressure changes.

Collecting and analyzing a small sample with equipment with a small interior volume allows for precise control and rigorous observation when the equipment is appropriately tailored for measurement. At elevated temperatures and pressures, the equipment may also be configured for effective operation over a wide temperature range and at high pressures. Selecting a small size for the equipment is advantageous for rugged operation because the heat transfer and pressure control dynamics of a smaller volume of fluid are easier to control then those of large volumes of liquids. That is, a system with a small exterior volume may be selected for use in a modular oil field services device for use within a wellbore. A small total interior volume can also allow cleaning and sample exchange to occur more quickly than in systems with larger volumes, larger surface areas, and larger amounts of dead spaces. Cleaning and sample exchange are processes that may influence the reliability of the microfluidic system 210, 310. That is, the smaller volume uses less fluid for observation, but also can provide results that are more likely to be accurate.

The minimum production pressure of the reservoir may be determined by measuring the saturation pressure of a representative reservoir fluid sample at the reservoir temperature. In a surface measurement, the reservoir phase envelope may be obtained by measuring the saturation pressure (bubble point or dewpoint pressures) of the sample using a traditional PVT view cell over a range of temperatures. Saturation pressure can be either the bubble or dewpoint of the fluid, depending upon the fluid type. At each temperature, the pressure of a reservoir sample is lowered while the sample is agitated with a mixer. This is done in a view cell until bubbles or condensate droplets are optically observed and is known as a Constant Composition Expansion (CCE). The PVT view cell volume is on the order of tens to hundreds of milliliters, thus using a large volume of reservoir sample to be collected for analysis. This sample can be consumed or altered during PVT measurements. A similar volume may be used for each additional measurement, such as density and viscosity, in a surface laboratory. Thus, the small volume of fluid used by microfluidic sensors of the present disclosure (approximately 1 milliliter total for measurements described herein) to make measurements may be highly advantageous.

In one or more embodiments, an optical phase transition cell may be included in a microfluidic PVT tool. It may be positioned in the fluid path line to subject the fluid to optical interrogation to determine the phase change properties and its optical properties. U.S. patent application Ser. No. 13/403,989, filed on Feb. 24, 2012 and United States Patent Application Publication Number 2010/0265492, published on Oct. 21, 2010 describe embodiments of a phase transition cell and its operation. Each of these applications is incorporated herein by reference in its entirety. The pressure-volume-temperature phase transition cell may contain as little as 300 μl, or less, of fluid. The phase transition cell detects the dew point or bubble point phase change to identify the saturation pressure while simultaneously nucleating the minority phase.

The phase transition cell may provide thermal nucleation which facilitates an accurate saturation pressure measurement with a rapid depressurization rate of from about 10 to about 200 psi/second. As such, a saturation pressure measurement (including depressurization from reservoir pressure to saturation pressure) may take place in less than 10 minutes, as compared to the saturation pressure measurement via standard techniques in a surface laboratory, wherein the same measurement may take several hours.

Some embodiments may include a view cell to measure the reservoir asphaltene onset pressure (AOP) as well as the saturation pressures. Hence, the phase transition cell becomes a configuration to facilitate the measurement of many types of phase transitions during a CCE.

In one or more embodiments, the densitometer 317, viscometer 319, a pressure gauge and/or a method to control the sample pressure with a phase transition cell may be integrated so that most sensors and control elements operate simultaneously to fully characterize a live fluid's saturation pressure. In some embodiments, each individual sensor itself (e.g., densitometer 317 or viscometer 319) has an internal volume of no more than 20 microliters (approximately 2 drops of liquid) and by connecting each in series, the total volume (500 microliters) to charge the system with live oil before each measurement may be minimized. In some embodiments, the fluid has a total fluid volume of about 1.0 mL or less. In other embodiments, the fluid has a total fluid volume of about 0.5 mL or less.

This configuration is substantially different than a traditional Pressure-Volume-Temperature (PVT) apparatus, but provides similar information while reducing the amount of fluid consumed for measurement. FIG. 3A is a schematic of one embodiment of a PVT apparatus for use downhole. In some embodiments, the PVT apparatus may be included into another measurement tool or may be standalone on a drill string or wire line.

The system's 210, 310 small dead volume (less than 0.5 mL) facilitates pressure control and sample exchange. In some embodiments, the depressurization or pressurization rate of the fluid is less than 200 psi/second. In some embodiments, the fluid is circulated through the system at a volumetric rate of no more than 1 ml/sec.

As mentioned above, the tool of the present disclosure may include a densitometer 317 (or analogous densitometer of fluid analyzer 308) to measure fluid density which, in some examples, may be used to calculate compressibility. The fluid compressibility, k, can be calculated by precisely measuring the fluid density while varying the pressure. The compressibility can be defined as the relative change in fluid density with the change in pressure as in the following equation:

$$k[p] = \frac{1}{\rho}\frac{\partial \rho}{\partial P} \quad (1)$$

FIGS. 4A to 5H show components of the densitometer 317. It should be understood that, although the example device is a configured to function as a densitometer, any suitable fluid analysis system may implement features analogous to those described in connection with the densitometer 317. For example, a microfluidic coriolis force meter may implement analogous isolation, electrical, structural, and/or vibrational features to those described in connection with densitometer 317.

Figure 4A:
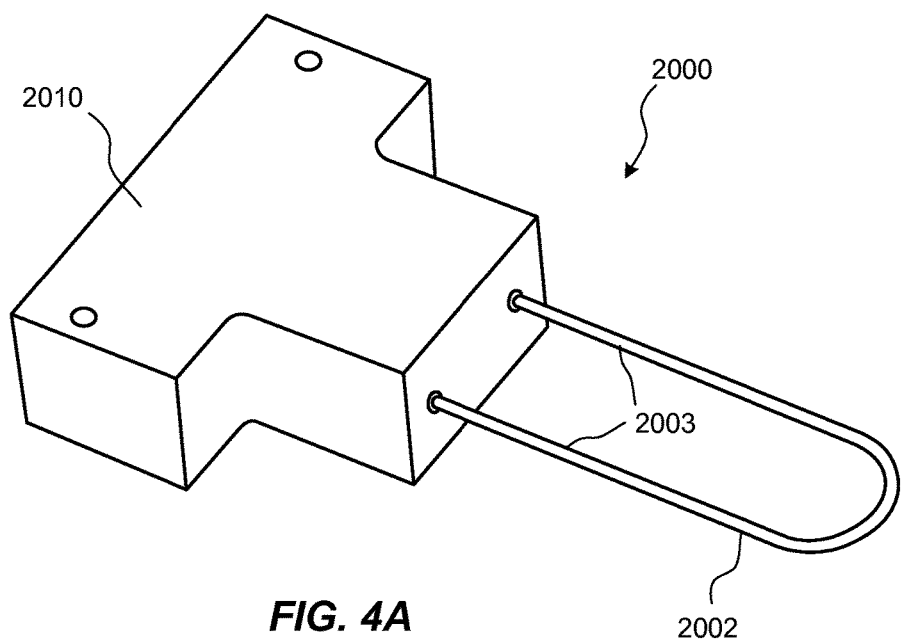
FIG. 4A shows a portion of a vibrating-tube densitometer.
Figure 4B:
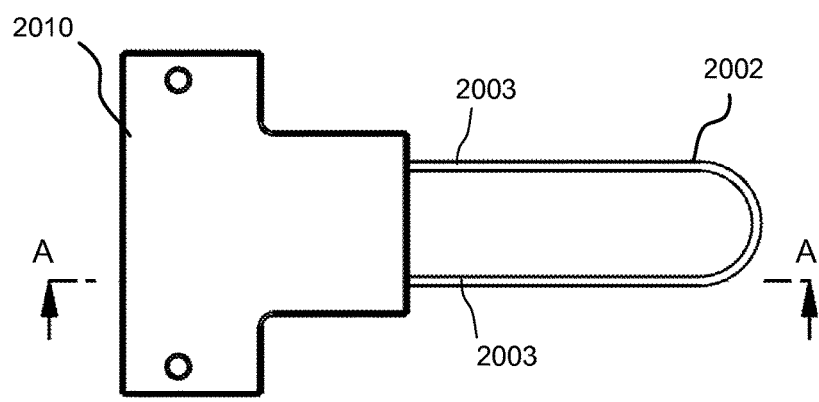
FIG. 4B shows a top view of the structure of FIG. 4A.

FIGS. 4A and 4B show a vibrating tube densitometer module 2000 of the densitometer 317 with integrated electrical isolation components. A U-shaped thin vibrating tube element 2002 functions as the vibrating element of the vibrating tube densitometer module 2000. A proximal end portion of the vibrating tube element 2002 is supported at a body block 2010, leaving the remaining portion of the vibrating tube element 2002 cantilevered to allow for the vibration utilized in the operation of the densitometer 2000. The proximal portion of the tube element 2002, which includes two open tube ends corresponding to two respective legs 2003, is hermetically sealed with respect to the body block 2010 to prevent sample fluids from leaking as they pass into and out of the tube element 2002.

Figure 4C:
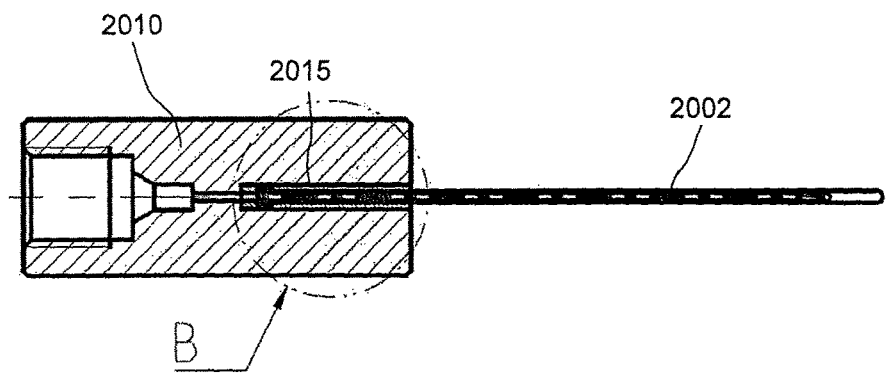
FIG. 4C shows a cross-sectional view corresponding to section A-A of FIG. 4B.
Figure 4D:
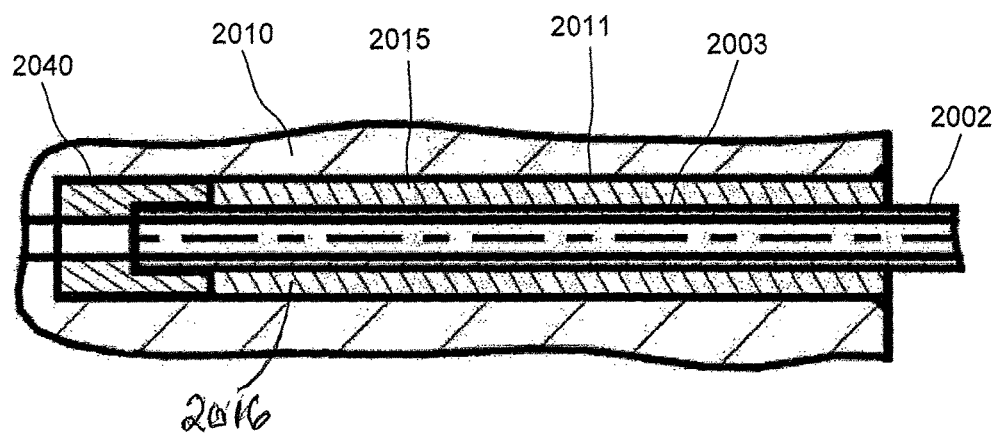
FIG. 4D shows an enlarged partial sectional view corresponding to section B of FIG. 4C.

Referring to the cross-sectional views of FIGS. 4C and 4D an electrical insulator 2015 couples the proximal end of each of the two legs of the vibrating tube element 2002 to the body block 2010. This coupling 2015 mechanically supports the vibrating tube element 2002 and simultaneously provides electrical insulation to prevent electrical currents from passing from the body block 2010 or other portion of the densitometer 2000 to the vibrating tube element 2002 and vice-versa, thereby electrically isolating the vibrating tube element 2002 from the body block 2010. This prevents electrical noise present in components such as conductive fluid delivery tubes and the body block 2010 from interfering with the electrical signals utilized with the vibrating tube element 2002 during density measurements.

As illustrated in FIG. 4D, the electrical insulator 2015 extends along the proximal end portion of the leg 2003 of the vibrating tube element 2002. The electrical insulator 2015 is formed of glass. In some examples, the electrical insulator 2015 is formed by glass frit bonding using doped glass powder. The doped glass powder has a low melting temperature (e.g., less than 450° C.) that will allow the doped glass powder to melt while avoiding melting of the body block 2010. Such powders may be obtained commercial from, for example, Asahi Glass Co., LTD of Tokyo, Japan.

Although in some examples, the electrical insulator 2015 is a single monolithic component, the electrical insulator 2015 shown in FIGS. 4C and 4D is formed of two components. In particular, the insulator 2015 is formed of a doped glass body 2016 and a base body 2040. It should be understood that the features corresponding to a cross section through the second leg 2003 are the same as the features described in connection with the cross section through the first leg 2003 illustrated in FIGS. 4C and 4D, although in other examples, the features may differ between the two sides.

The doped glass powder is formed into a near-shape glass bead by compression molding. This near-shape bead is then placed in the position in the block 2010 where it is to provide an electrically insulative hermetic seal. In the illustrated example, the doped glass bead is placed into a channel 2011 in the block 2010 and corresponds to the general shape and position as the insulator 2015. After the bead is placed in the channel 2011, the vibrating tube element 2002 is inserted into the channel 2011 and into the bead. The structure is then heated to the melting point of the doped glass bead. During the heating and subsequent cooling, the doped glass will bond to the metal and became solid, thereby securing the tube 2002 in place relative to the block 2010.

Referring to the example of FIG. 4D, when the doped glass is in a liquid or non-rigid state during the melting process, the vibrating tube element 2002 is maintained in its position spaced apart from the annular channel wall 2011 by the base bodies 2040 which function as jigs, receiving the respective ends of the legs 2003. The base bodies 2040 in the illustrated example are formed of an electrically insulative material (e.g., glass or ceramic) that has a melting temperature substantially higher than the melting temperature of the doped glass utilized to form the doped glass body 2016. As such, when the densitometer module 2000 is heated to melt the doped glass to form the insulator doped glass body 2016, the base bodies 2040 remain solid, thereby retaining adequate structure to maintain the insulator doped glass body in its position spaced apart from the channel 2011 of the block 2010 until the doped glass has cooled and solidified to produce the hermetically sealed solid insulator structure 2015. The base body 2040 may also be utilized to block potential flow of the melted doped glass during the heating process.

Figure 5A:
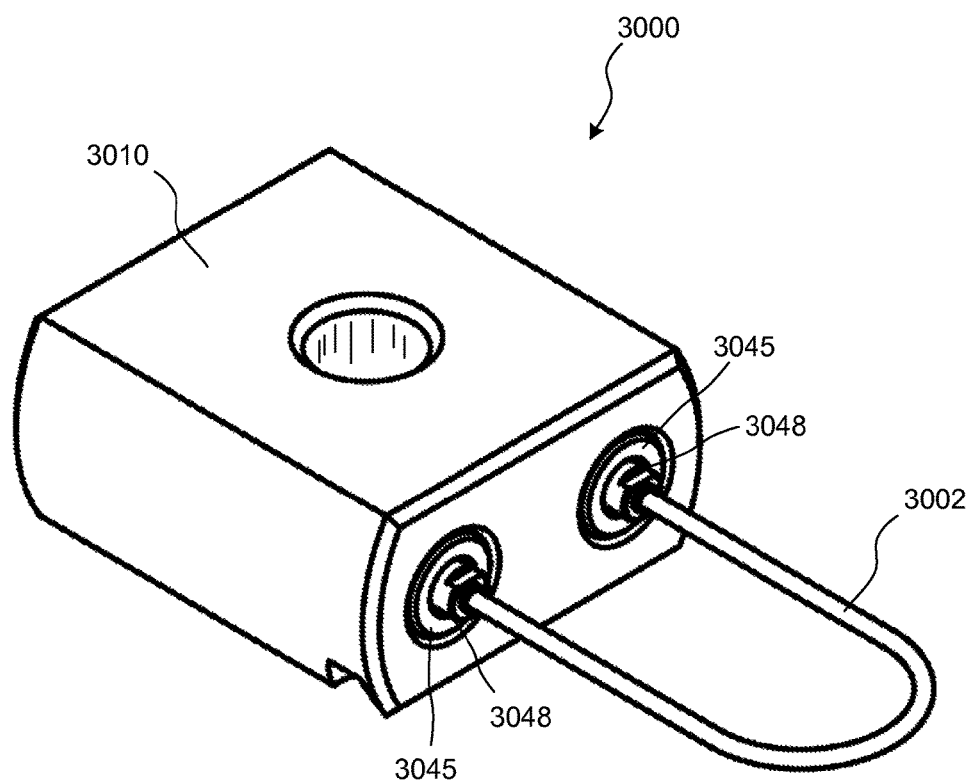
FIG. 5A shows a portion of a vibrating-tube densitometer.
Figure 5B:
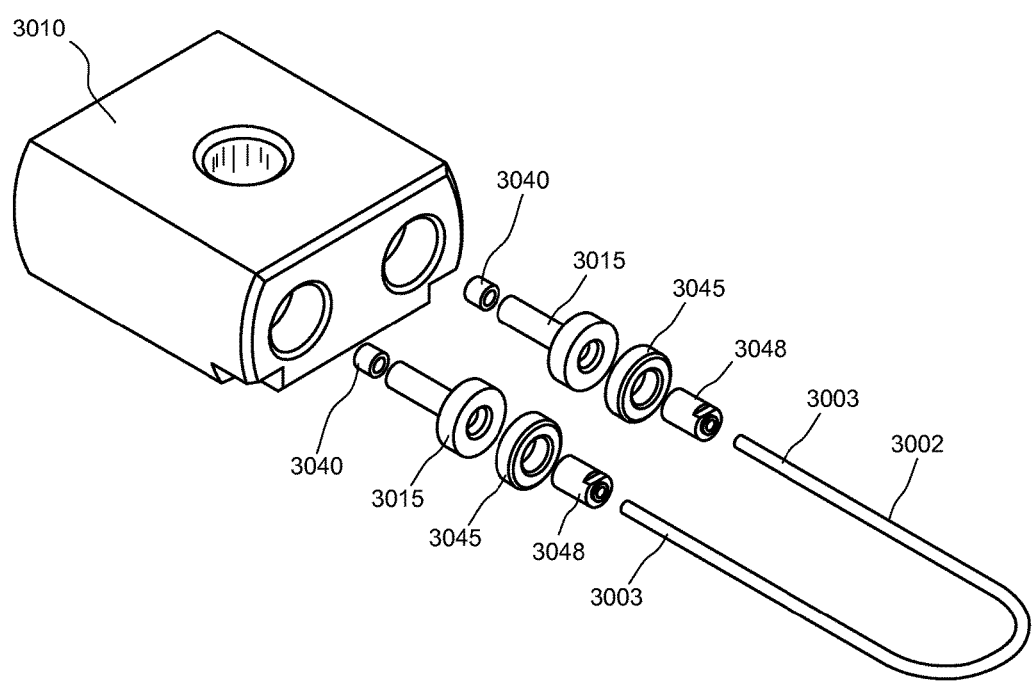
FIG. 5B shows an exploded view of the structure of FIG. 5A.
Figure 5C:
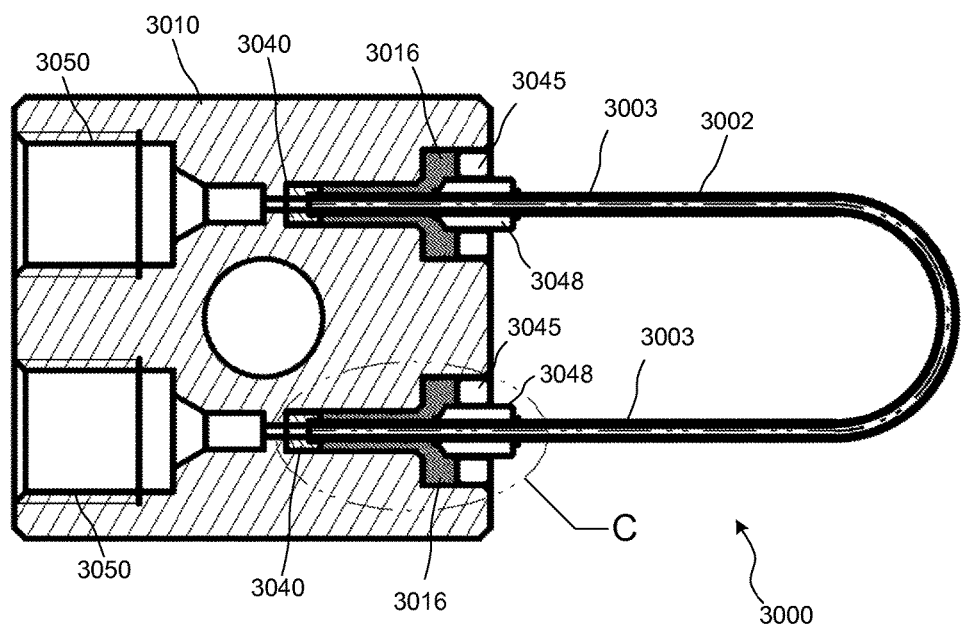
FIG. 5C shows a cross-sectional view of the structure of FIG. 5A.

FIGS. 5A and 5B show a densitometer module 3000 that is analogous to the densitometer module 2000 except to the extent described otherwise.

The densitometer module 3000 differs in the structure of the base block 3010 and the insulator structure. Referring to the exploded view of FIG. 5B and the cross-sectional views of FIGS. 5C and 5D, the channel 3011 has an enlarged section 3012 with a diameter that is larger than the remainder of the channel 3011. This enlarged section 3012 receives a corresponding enlarged portion 3017 of the doped glass body 3016.

Further, in addition to the base body 3040 and the doped glass body 3016, the electrically insulating coupling 3015 further includes a cap body 3045, which functions as a second jig disposed at the end of the doped glass body 3016 opposite the base body 3040. This two jig configuration—i.e., the base body 3040 and the cap body 3045—serve to stably support the leg 3003 of the vibrating tube element 3002 during the melting of the doped glass, and may also be utilized to resist flow of the liquefied or non-solid doped glass from its intended position during the heating process.

In the illustrated example, the cap body 3045 further receives and supports a mass block 3048, which is coupled to the respective leg 3003 of the vibrating tube element 3002. The mass block 3048 may be secured to the leg 3003 via the adhesion of the doped glass of the doped glass body 3016 and/or any other suitable coupling mechanism. In some examples, the mass block 3048 is present to provide additional vibrational isolation of the vibrating tube 3002 to improve performance during operation of the vibrating tube densitometer 3000 to measure fluid density.

In some examples, the presence of the mass block 3048, in addition to the rigid connection of the mass block 3048 to the vibrating tube element 3002, causes a standing wave node location at the location of the mass block 3048 during the vibration of the vibrating tube element 3002. In this regard, the mass of the block 3048 coupled with the fact that its location corresponds to the vibrational node allows for electrical connections be made without altering the vibrational properties of the vibrating tube element 3002. For example, the electrical connections may be made directly to the electrically conductive mass blocks 3048. Since the mass blocks 3048 are electrically coupled to the vibrating tube element 3002, applying the electrical leads to the mass blocks 3048 provides a mechanism to apply an excitation current and/or measure vibrational response without having the physical electrical connection adversely impact the performance of the device. In particular, the for example, this structure allows for connecting the electrical leads without altering the resonance of the tube 3002.

As with the base bodies 2040 described above, the base bodies 3040 and the cap bodies 3045 in the illustrated example are formed of an electrically insulative material (e.g., glass or ceramic) that has a melting temperature substantially higher than the melting temperature of the doped glass utilized to form the doped glass body 3016. As such, when the densitometer 3000 is heated to melt the doped glass to form the doped glass body 3016, the cap bodies 3045 remain solid, thereby retaining adequate structure to maintain the insulator 2015 in its position spaced apart from the channel 3011 of the block 2010 until the doped glass has cooled and solidified to produce the hermitically sealed solid insulator structure 2015. It should be understood that the various instances of the base bodies 2040, 3040 and cap bodies 3045 in any given example may be formed of the same or different materials relative to each other.

Figure 5D:
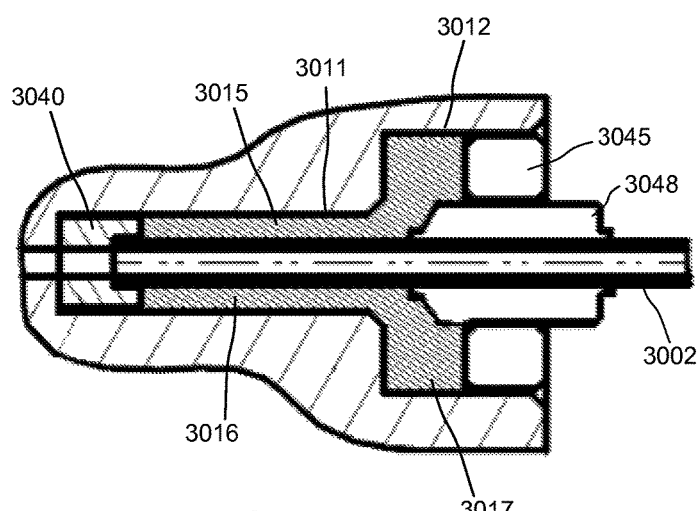
FIG. 5D shows a partial sectional view corresponding to section C of FIG. 5C.
Figure 5E:
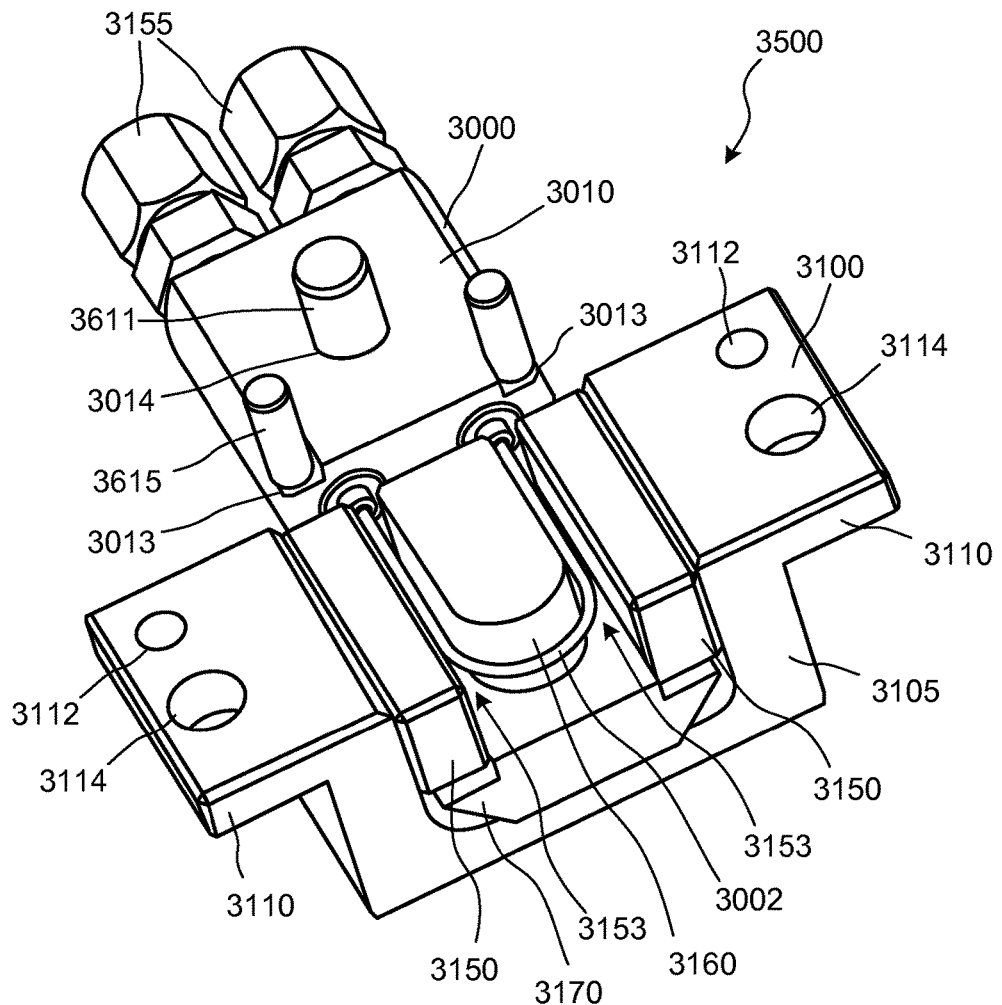
FIG. 5E shows a subassembly incorporating the structure of FIG. 5A.

FIG. 5E shows a densitometer subassembly 3500 that includes the vibrating tube densitometer module 3000. The subassembly 3500 further includes high-pressure sealed tube fittings 3155 that mate with receptacles 3050, which are visible in FIG. 5C, to couple a metal flowline to the sensor module 3000 in order to deliver sample fluids to and away from the vibrating tube element 3002 for density measurements. Because of the insulating coupling 3015, any electrical noise that may be present in the flowline or other conductive structures is isolated from the vibrating tube element 3002 to prevent such noise from interfering with the density measurement during operation of the densitometer. At the same time, the insulating coupling 3015 maintains a hermetic seal between the flowline and the vibrating tube 3002 under operating conditions of the densitometer. The same features apply with regard to the insulating coupling 2015.

The densitometer subassembly 3500 further includes a magnet unit 3100 that includes a mounting bracket 3105 having mounting flanges 3110. The mounting flanges 3110 include recesses 3112 to receive alignment pins, and holes 3114 to receive fasteners 3610 to locate and secure the magnet unit 3100 to a base chassis 3605, as shown in further detail in connection with FIG. 5F. Similarly, the base block 3010 includes recesses 3013 to receive locating pins 3615, and a hole 3014 to receive a fastener 3611 to locate and secure the densitometer module 3000 to the base chassis 3605. Although various fasteners and locating devices may be described herein, it should be understood that any suitable assembly and/or manufacturing methods may be employed, and the present disclosure is in no way limited to the specific examples shown and described.

The magnet unit 3100 further includes a pair of magnets 3150 disposed on opposite sides of the vibrating tube element 3002 and adjacent to respective legs 3003 of the vibrating tube element 3002. Magnets 3150 are oriented in the same polarized direction. As such, these two magnets 3150 are magnetically coupled in series. The magnets 3150 in the illustrated example are permanent magnets that are high temperature-resistant.

There is also a yoke 3160 disposed between the two legs 3003 of the vibrating tube element 3002. The yoke acts to optimize the magnetic field of the magnets 3150 acting on the vibrating tube 3002. The yoke 3160 and the mounting bracket 3105 are formed of a soft magnetic material such as a ferrous magnetic material The two magnets 3150, the yoke 3160, the mounting bracket 3105, and two gaps 3153 form a magnetic circuit in the illustrated example. The gaps 3153 may be filled with air or any other suitable medium and are disposed between the yoke 3160 and a respective magnet 3150 for accommodating the legs 3003 of the vibrating tube 3002.

Magnetic flux travels through the magnetic mounting bracket 3105 to the magnet 3150 and through gap 3153 resulting in a closed-loop magnetic circuit. In this regard, the element 3105 is not only a mounting bracket but also a magnetic flux path to enhance permeance of the magnetic circuit.

Figure 5F:
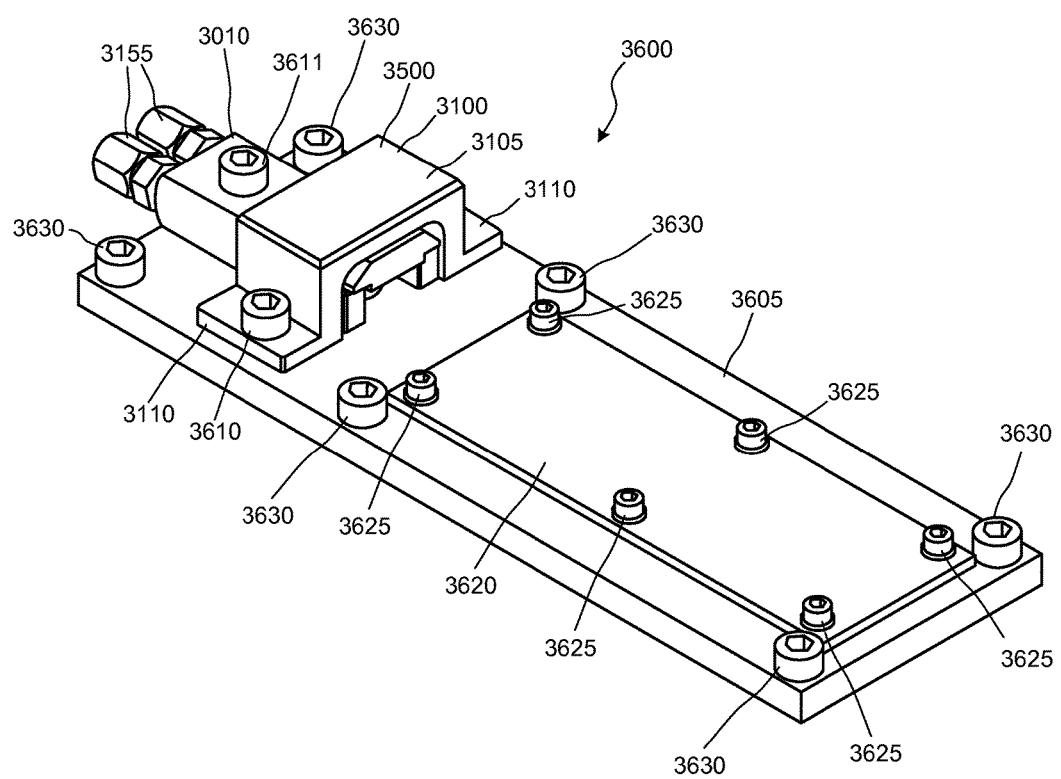
FIG. 5F shows an assembly incorporating the subassembly of FIG. 5E.

The magnets 3150 and the yoke 3160 are mounted to a block 3170 which is attached to the mounting bracket 3105. The block 3170 acts to secure and locate the magnets 3150 and yoke 3160 relative to each other and, as a result of the various components being mounted to the base chassis 3605 as shown in FIG. 5F, relative to the vibrating tube element 3002. This spacing and locating allows the magnets 3150 and yoke 3160 to act on the vibrating tube 3002 without coming into contact with the tube 3002 as it vibrates during density measurements. It should be understood that although an example of a magnet configuration is provided in connection with FIG. 5E, other magnet configurations may be provided. For example, for different resonances, different magnet positioning and arrangement may be provided. Some examples do not employ a yoke. Some examples include a single magnet or more than two magnets.

FIG. 5F shows a densitometer assembly 3600 that incorporates the subassembly 3500. In particular, the subassembly 3500 is mounted to the base chassis 3605 via fasteners 3610 and 3600 and the locating pins as discussed above. The assembly 3600 further includes a sensor front end circuit board 3620. The front end circuit board 3620 is mounted to the base chassis 3605 via fasteners 3625, and the base chassis 3605 is attached to a base tool via fasteners 3630. As with the other fasteners 3610 and 3611 described above, the fasteners 3625 and 3630 may be bolts or any other suitable fasteners.

The tubing 2002, 3002 may have an outer diameter of 1 mm or less in some non-limiting examples. The tubing 2002 may be made of stainless steel, Hastelloy, medical grade tubing, etc. In some examples, the tubing 2002 and/or other metallic components may be made of spring metal such as SPRON, developed by Seiko Instruments Inc.

The electrical isolation structures illustrated, for example, in FIGS. 4D and 5D function to fluidically and hydraulically connect the metal tubes 2002 and 3002 while maintaining electrical isolation of the tubes 2002 and 3002 with respect to the inlet tubes and other conductive structures external to the tubes 2002 and 2003.

In some examples, the block 2010, 3010 is metal (e.g., aluminum or stainless steel), although the block may be formed of any other suitable material.

Referring again to FIG. 5E, the vibrating tube element 3002 mounted in the body block 3010 and wrapped about a yoke 3160 and between magnets 3150 such as, for example, SmCo permanent magnets, wherein an alternating current is driven through the tube element 3002 and the resulting Lorentz force provides actuation to drive the tube 3002 in a torsional mode and the resulting electromagnetic field (EMF) (Faraday's law) is proportional to the tube velocity.

It is noted that motion may be monitored by measuring the small EMF voltage that develops due to Faraday's law. Example embodiments of the densitometer are operable to high pressures up to 15,000 psi or more and high temperatures up to 150° C. or more for determining measurements in a tube having an outer diameter approximate 1/32" along with a fluid sampling volume of less than 20 microliters. It is noted that temperatures in some oilfield applications may reach 150° C. (it is noted the temperatures could be as high as 350° C.) along with pressures of 15,000 psi (it is also noted the pressures could be as high as 35,000 psi). Further, the diameter of the tube can be greater or less and the fluid sampling volume may be up to, for example, 1000 microliters. Further still, the tubes used in this densitometer configuration. by non-limiting example are made of stainless steel or other related materials having similar properties. However, other types of metals may be used (for example, titanium, nickel and related alloys). It is further noted that the above-described glass insulator configurations are also able to withstand the aforementioned pressure and temperature conditions, such as may be found, for example, downhole during open-hole operations.

In the illustrated example, each leg 2003, 3003 of the tube 2002, 3002 is of approximately length 4.5 cm. The end of the tube 2002, 3002 may be bent into a half circle of an approximate diameter of 1 cm so as to create an approximate total internal volume of approximately 20 μl (as note above the total internal volume may be approximately up to 1000 μl. However, alternative shapes and dimensions for the tube may be provided, such as a straight tube or a tube with differing bends. The body block 2010, 3010 may be secured in the downhole housing by any suitable fastening mechanism (e.g., screws, adhesive, soldering, welding, brazing, etc.) and in some examples electrically isolated from the downhole housing.

A typical high pressure fluidic system connects a metal flowline to the electrical ground plane, thereby introducing stray impedances which would alter if not completely ruin the signal used here to measure fluid density. Thus, the glass insulators 2015, 3015 are provided to electrically isolate the two coupled tubes, along with being capable of operating in high shock and high temperature device conditions. In contrast with some other potential solutions, the electrical isolation structure of, e.g., FIGS. 4D and 5D provide electrical isolation without adding an unacceptable amount of dead volume. Since these sensors are considered to be microfluidic, the addition of a significant amount of dead volume (e.g. greater than a few, e.g., 3, microliters) would render the sensor inoperable in some intended microfluidic applications, or would require greater flushing volume.

Figure 5G:
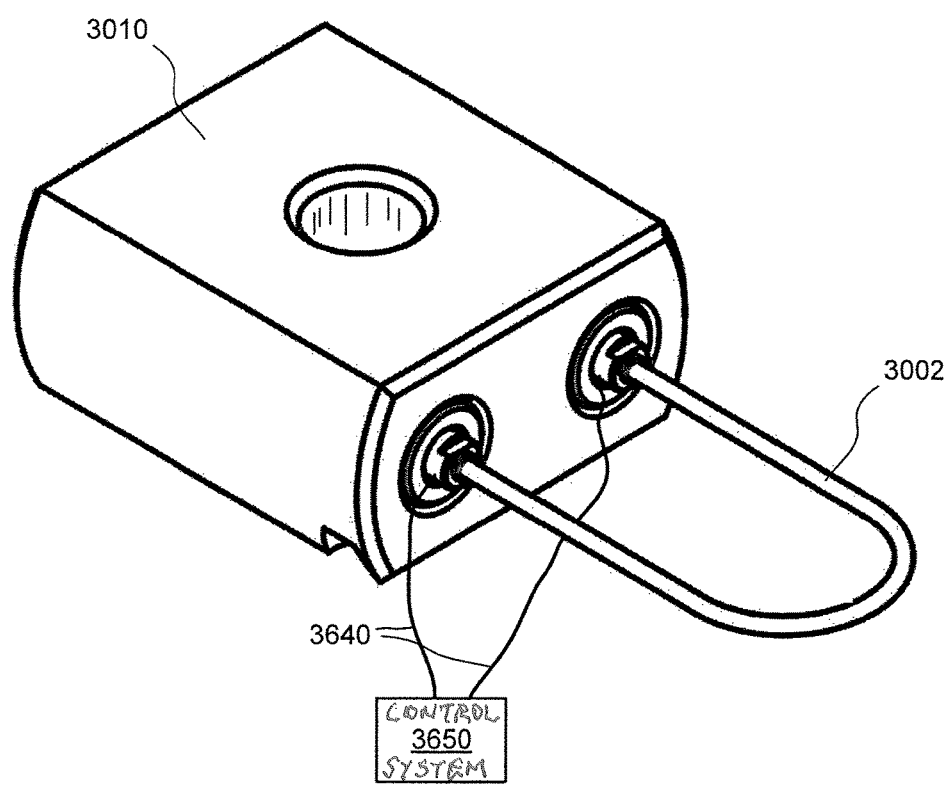
FIG. 5G shows the structure of FIG. 5A with an electrical control system and electrode leads in place.

Electrical connections to the tube 3002 may be provided in the form of, referring to FIG. 5G, wires 3640, may be soldered or otherwise attached to be in electrical communication with respective legs of the tube 3002. As indicated above, the connection of the electrical leads at the mass blocks 3048 in the illustrated example allows for an electrical connection that does not mechanically affect the vibrational properties of the tube 3002 by, for example, altering the relevant resonance frequency of the tube 3002 in the absence of such connection.

Figure 5H:
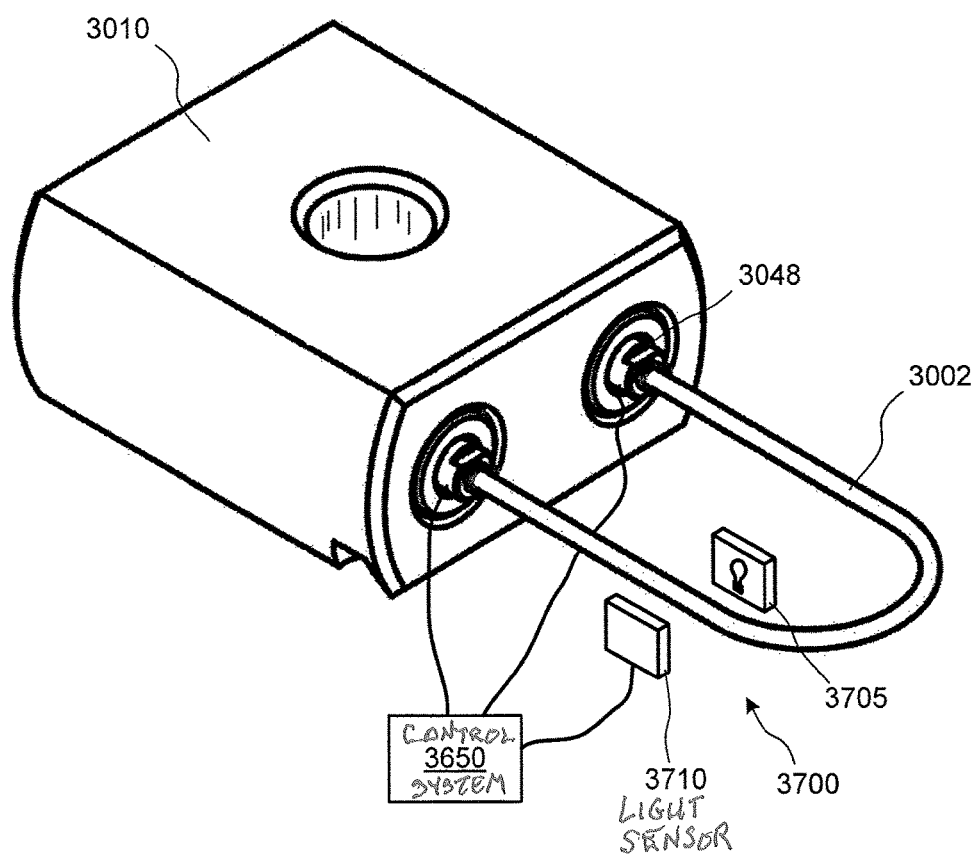
FIG. 5H shows the structure of FIG. 5A with an electrical control system and an optical detection system.

An electrical control system 3650, which may be, for example, front end circuit board 3620, is connected to the electrical connections 3640 to provide the voltage and current across the electrical leads and corresponding legs of the tube element 3002 to induce the aforementioned vibrations. The control system 3650 is also configured to measure the resulting EMF, which is in turn used to determine the density of the fluid present in the vibrating tube element 3002. In this regard, the EMF reflects the resonant frequency of the tube 3002 together with the sample fluid inside the tube 3002. Since this frequency varies as a function of the density of the sample fluid in the tube 3002, it provides a mechanism by which to measure the density of the fluid. It should be understood that instead of a single unit 3650 that drives the current and senses the EMF, separate systems may be provided. Moreover, alternatively or additionally, the frequency of the vibrating tube 3002 may be measured by any other suitable mechanism, e.g., using optical detection. FIG. 5H shows an example of an optical detection system 3700 including a light source 3705 and a light sensor 3710. In this arrangement, the signal generated from the light sensor 3710 varies as a function of the frequency at which the tube 3002 vibrates. Accordingly, the control system 3650 can process the signal to determine the frequency.

It is further noted that in addition to the vibration, the control system of the illustrated example factors in temperature and pressure in determining the density of the fluid.

Additional details of the operation of the densitometer configurations 2000 and 3500 may be found in U.S. Patent Application Publication No. 2010/0268469, which is incorporated herein by reference in its entirety and provides an analogous densitometer structure and function, but without, for example, the glass isolator configuration of the present application.

Further details of using the PVT apparatus in conjunction with a wellbore tool and methods for implementing the PVT apparatus are described in U.S. Patent Application Publication No. 2014/0260586 and PCT International Publication No. WO 2014/158376, each of which is incorporated herein by reference in its entirety.

The methods and processes described above such as, for example, operation of valves and pistons and the performance of the various described fluid analyses, may be performed by a processing system. The processing system may correspond at least in part to element 3650 described above. The term "processing system" should not be construed to limit the embodiments disclosed herein to any particular device type or system. The processing system may include a single processor, multiple processors, or a computer system. Where the processing system includes multiple processors, the multiple processors may be disposed on a single device or on different devices at the same or remote locations relative to each other. The processor or processors may include one or more computer processors (e.g., a microprocessor, microcontroller, digital signal processor, or general purpose computer) for executing any of the methods and processes described above. The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

The methods and processes described above may be implemented as computer program logic for use with the computer processor. The computer processor may be for example, part of a system such as system 100 described above. The computer program logic may be embodied in various forms, including a source code form or a computer executable form. Source code may include a series of computer program instructions in a variety of programming languages (e.g., an object code, an assembly language, or a high-level language such as C, C++, Matlab, JAVA or other language or environment). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processing system may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Any of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language or a high-level language such as C, C++ or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

Although a few example embodiments have been described in detail above, those skilled in the art will readily appreciate that many modifications are possible in the example embodiments without materially departing from embodiments disclosed herein. Accordingly, all such modifications are intended to be included within the scope of this disclosure.

What is claimed is:

1. A device for measuring a property of a fluid sample, the device comprising:
    a tube configured to receive the fluid sample;
    a base block supporting the tube;
    a magnet configured to apply a magnetic field to the tube;
        an excitation source configured to generate vibration of the tube when the fluid sample is received in the tube by circulation of an electrical current along a portion of the tube and interaction of the electrical current to at least one magnetic field produced by the magnet;
    a vibration sensor configured to measure a signal corresponding to a vibration frequency of the tube;
    an electrical isolator comprised of glass and separate and distinct from the base block, wherein the tube is hermetically sealed to the base block via the electrical isolator and electrically isolated from the base block via the electrical isolator, and wherein the base block has an internal channel and the electrical isolator is disposed in the internal channel of the base block; and
    a mass block that is electrically coupled to the tube to provide an electrical connection between the excitation source and the tube, wherein the mass block is rigidly coupled to the tube such that the mass block provides a standing wave vibrational node of the tube when the excitation source generates the vibration of the tube, and wherein the mass block is electrically isolated from the base block by the electrical isolator.

2. The device of claim 1, further comprising an electrical lead attached to the mass block and configured to convey an excitation current from the excitation source to the tube via the mass block.

3. The device of claim 2, further comprising:
    a second electrical isolator comprised of glass and separate and distinct from the base block, wherein first and second ends of the tube are hermetically sealed to the base block via the electrical isolator and the second electrical isolator and electrically isolated from the base block via the electrical isolator and the second electrical isolator;
    a second mass block that is electrically coupled to the tube to provide a second electrical connection between the excitation source and the tube, wherein the second mass block is rigidly coupled to the tube such that the second mass block provides a standing wave vibrational node of the tube when the excitation source generates the vibration of the tube, wherein the second mass block is isolated from the base block by the second electrical isolator; and
    a second electrical lead attached to the second mass block, wherein the electrical lead, the mass block, the tube, the second mass block, and the second electrical lead form an electrical circuit via which the excitation source is configured to apply the excitation current across the tube.

4. The device of claim 1, wherein the device is configured to measure a density of the fluid sample.

5. The device of claim 1, wherein the device is configured to measure a flow rate of the fluid sample.

6. The device of claim 1, wherein the excitation source and the vibration sensor are a single component.

7. The device of claim 1, wherein the electrical isolator comprised of two glass elements, each corresponding to a respective end of the tube.

8. The device of claim 1, wherein the glass is a doped glass.

9. The device of claim 8, wherein the doped glass has a melting point that is lower than respective melting points of the base block and the tube.

10. The device of claim 9, further comprising a jig configured to maintain a position of the tube relative to the base block when the doped glass is melted.

11. The device of claim 10, wherein the jig is comprised of a glass material having a melting point that is higher than the melting point of the doped glass.

12. The device of claim 1, further comprising a processor configured to determine a resonant frequency of the tube based on the signal measured by the vibration sensor.

13. The device of claim 1, wherein the device is configured to operate downhole in a wellbore.

14. The device of claim 1, further comprising a yoke configured to alter the magnetic field produced by the magnet when the magnetic field is applied to the tube.

15. The device of claim 14, wherein the magnet is comprised of two separate magnetic elements and the yoke is disposed between the two separate magnetic elements.

16. The device of claim 14, wherein
the tube is a U-shaped element having two legs,
the yoke is disposed between the two legs.

17. The device of claim 16, wherein
the magnet is comprised of two separate magnetic elements,
the yoke is disposed between the two separate magnetic elements, and
each leg of the U-shaped element is disposed between the yoke and a respective one of the magnetic elements.

18. The device of claim 1, wherein the electrical isolator is disposed between the mass block and the base block.

19. The device of claim 1, wherein the electrical isolator includes a recess for receiving the mass block.

20. The device of claim 1, wherein the electrical isolator and the mass block both include respective passageways through which the tube extends.

21. A system for characterizing a fluid, comprising:
a phase transition cell configured to receive the fluid;
a piston configured to control pressure of the fluid;
a pressure gauge configured to measure the pressure of the fluid and to provide information to control the piston; and
a fluid analyzer configured to measure a property of the fluid, the analyzer comprising
a tube configured to receive a fluid sample,
a base block supporting the tube,
a magnet,
an excitation source configured to generate vibration of the tube when the fluid sample is received in the tube by circulation of an electrical current along a portion of the tube and interaction of the electrical current to at least one magnetic field produced by the magnet,
a vibration sensor configured to measure a signal corresponding to vibrations of the tube,
an electrical isolator comprised of glass and separate and distinct from the base block, wherein the tube is mounted to the base block via the electrical isolator and electrically isolated from the base block via the electrical isolator, and wherein the base block has an internal channel and the electrical isolator is disposed in the internal channel of the base block, and
a mass block that is electrically coupled to the tube to provide an electrical connection between the excitation source and the tube, wherein the mass block is rigidly coupled to the tube such that the mass block provides a standing wave vibrational node of the tube when the excitation source generates the vibration of the tube, and wherein the mass block is electrically isolated from the base block by the electrical isolator.

22. The device of claim 21, wherein the device is configured to operate downhole in a wellbore.

23. The device of claim 21, wherein the fluid analyzer is a vibrating tube densitometer.

24. A device for measuring a property of a fluid sample, the device comprising:
a tube having first and second ends, the tube configured to receive the fluid sample;
a base block supporting the tube;
a magnet configured to apply a magnetic field to the tube;
an excitation source configured to generate vibration of the tube when the fluid sample is received in the tube by circulation of an electrical current along a portion of the tube and interaction of the electrical current to at least one magnetic field produced by the magnet;
a vibration sensor configured to measure a signal corresponding to a vibration frequency of the tube;
two electrical isolators comprised of glass and separate and distinct from the base block, wherein the first and second ends of the tube are hermetically sealed to the base block via the two electrical isolators and electrically isolated from the base block via the two electrical isolators, and wherein the base block has two internal channels and the two electrical isolators are disposed in the two internal channels of the base block; and
two mass blocks that are electrically coupled to the tube to provide electrical connections between the excitation source and the tube, wherein the two mass blocks are rigidly coupled to the tube such that the two mass blocks each provide a standing wave vibrational node of the tube when the excitation source generates the vibration of the tube, and wherein the two mass blocks are electrically isolated from the base block by the two electrical isolators.

* * * * *